United States Patent
Hsu (10) Patent No.: US 9,395,279 B2
(45) Date of Patent: Jul. 19, 2016

(54) METHOD FOR EVALUATION OF CABLE AGING DEGRADATION BASED ON SLICE SAMPLING

(71) Applicant: ATOMIC ENERGY COUNCIL—INSTITUTE OF NUCLEAR ENERGY RESEARCH, Taoyuan County (TW)

(72) Inventor: Yao-Tung Hsu, Taoyuan County (TW)

(73) Assignee: Atomic Energy Council—Institute of Nuclear Energy Research, Taoyuan County (TW)

(*) Notice: Subject to any disclaimer, the term of this patent is extended or adjusted under 35 U.S.C. 154(b) by 235 days.

(21) Appl. No.: 14/297,794

(22) Filed: Jun. 6, 2014

(65) Prior Publication Data

US 2015/0028885 A1   Jan. 29, 2015

(30) Foreign Application Priority Data

Jul. 23, 2013  (TW) .............................. 102126375 A (51) Int. Cl.
| | | |
|---|---|---|
| *G01R 31/02* | (2006.01) | |
| *G01N 27/04* | (2006.01) | |
| *G01N 1/04* | (2006.01) | |
| *G01R 31/12* | (2006.01) | |
| *G01N 1/06* | (2006.01) | |
| *G01N 1/08* | (2006.01) | |
| *G01R 27/26* | (2006.01) | |

(52) U.S. Cl.
CPC .. *G01N 1/04* (2013.01); *G01N 1/06* (2013.01); *G01N 1/08* (2013.01); *G01R 31/12* (2013.01); *G01R 31/1263* (2013.01); *G01R 31/1272* (2013.01); *G01N 2203/0298* (2013.01); *G01R 27/2617* (2013.01)

(58) Field of Classification Search
CPC .. G01R 31/021; G01R 31/12; G01R 31/1263; G01R 31/1272; G01R 27/2617; G01N 1/04; G01N 1/06; G01N 1/08
USPC ......... 324/557, 551, 544, 543, 541, 539, 537, 324/500
See application file for complete search history.

(56) References Cited

U.S. PATENT DOCUMENTS

| | | | | |
|---|---|---|---|---|
| 4,136,920 A | * | 1/1979 | Scholtholt ............ | H01R 4/2462 439/395 |
| 4,721,916 A | * | 1/1988 | Hanasawa .......... | G01R 31/1272 324/520 |
| 5,225,814 A | * | 7/1993 | Choi .................... | G01R 31/021 324/539 |
| 6,359,443 B1 | * | 3/2002 | Endo ..................... | B60N 2/002 324/503 |

(Continued)

FOREIGN PATENT DOCUMENTS

| | | |
|---|---|---|
| CN | 101738572 A | 6/2010 |
| CN | 102096031 A | 6/2011 |
| TW | I237123 B | 8/2005 |

*Primary Examiner* — Hoai-An D Nguyen
(74) *Attorney, Agent, or Firm* — Rosenberg, Klein & Lee (57) ABSTRACT

A method for evaluation of cable aging degradation based on slice sampling is revealed. An insulation layer of a cable is aged or degraded from the outside in under influence of high temperature, liquid immersion, radiation exposure, or other factors. The present invention gets slices as samples of the cable by cutting from the outside in. Then related tests including dielectric withstand test, insulation resistance measurement, elongation test, etc. are carried out. Besides the state of cable aging degradation being of the slice being found out, different positions in the insulation layer such as an outer layer, a middle layer and an inner layer can also be evaluated.

8 Claims, 7 Drawing Sheets

(56) References Cited

U.S. PATENT DOCUMENTS

| | | | |
|---|---|---|---|
| 7,992,449 B1 | 8/2011 | Mahmoud | |
| 2004/0160331 A1* | 8/2004 | Chiu | G01R 31/021 340/673 |
| 2005/0268734 A1 | 12/2005 | Watkins, Jr. et al. | |
| 2009/0267612 A1* | 10/2009 | Shimamura | E02F 9/24 324/537 |
| 2011/0210750 A1* | 9/2011 | Medelius | H01B 1/04 324/543 |
| 2012/0176243 A1* | 7/2012 | Andersen | G08B 13/186 340/568.1 |
| 2015/0048842 A1* | 2/2015 | Ngo | G01R 29/08 324/537 |

* cited by examiner

METHOD FOR EVALUATION OF CABLE AGING DEGRADATION BASED ON SLICE SAMPLING

FIELD OF THE INVENTION

The present invention relates to a method for evaluation of cable aging degradation, especially to a method for evaluation of cable aging degradation based on slice sampling by which an insulation layer of a cable is sliced gradually to get slices with different depths in the cable. Then the cable aging degradation is evaluated according to different aging degradation state of the slices with different depths in the cable.

BACKGROUND OF THE INVENTION

Electricity is indispensable in our daily life. The power outage incurred losses of households and industries. To ensure smooth operation of power network, each process of the power network including power generation, power transmission and power application should be monitored properly.

Within the power network, aging degradation of the cable is one of the important monitored items. Cables are used to carry electric currents and transmit power. Thus they should be durable to various environmental factors such as sun, wind, rain, immersion in seawater, or high-dose radiation in area around nuclear power plants. However, the service life and the insulation the cable provided is significantly decreased under influence of these factors. This poses a serious challenge for maintenance and management of the cable.

In an environment with high temperature, oxidation-resistant material on surface of the cable is gradually degraded; and in a humid environment, void characteristics in insulation materials such as size and density are also changed. As to an environment with radiation, the insulation materials are getting easier to be invaded by water. There is a rapid reduction of the resistance of the insulation materials.

Thus there is an urgent need to provide a method for precise detection of cable aging degradation and further preventing the cable from breaking without any signs and early warning.

Refer to Taiwanese Pat. Pub. No. TW 1237123, a method for detecting degradation of direct current cable is revealed. The method simples the insulation parameter of the direct current cable by a fixed cycle during a sampling period and builds up a trend table by the value sampled so as to judge the variation trend of the insulation parameter of the direct current cable. When the insulation parameter variation is increased dramatically in unit time, the degradation state of the cable is determined as seriously degraded and a warning signal is generated for replacement of the cable.

In this patent, the degradation detection of the cable is by using leakage current of the cable as sample and converting the leakage current into insulation parameter within a period of time. Thus the degradation state of the cable is determined. The method is unable to detect degradation state of samples obtained at different depth in the cable.

Refer to Chinese Pat. App. No. 200810202541.7, a method for testing service life of solid-insulated medium voltage power cable is revealed. Through accelerated water treeing test, 14-day heat/load cycle test, step-up breakdown voltage test at power frequency, step-up breakdown voltage test for measurement of impulse voltage, the statistics of the growth development and the density detection of water tree inside insulation part, electrical tests, and structural detection, a curve showing breakdown voltage test at power frequency changing along with the time of the accelerated water treeing test is obtained. The quality and the service life of the cable can be evaluated according to the curve.

The breakdown voltage test is a common test. However, the breakdown voltage test is carried out on expensive high voltage equipment. Yet the high voltage equipment is not common in general labs.

Refer to CN 201010595007.4, an apparatus for testing aging resistance and water tree resistance of medium voltage power cable is disclosed. The tests are also carried out by breakdown voltage, as the above patent.

Refer to U.S. Pat. No. 7,992,449, a method for assessment of cable strength and residual life is revealed. The method includes steps of random sampling of individual cable wires, mechanically testing the sampled wires, and determining residual life of cable wires according to stress-strain curves. The cable is divided into 8 uniformly spaced sectors, thus forming a typical eight-wedge pattern. The procedure involves inserting and driving the wedges into the wires along a respective wedge line resulting in a plurality of peripheral wedge openings. Instead of the degraded rubber material outside, the sampling target is wire.

Refer to US 20050268734, an electrical condition monitoring method for polymers is disclosed. The method utilizes measurements of electrical resistivity of an age sensor disposed in an electrical cable. The method is also unable to detect aging and degradation of positions at different depths state in the cable.

SUMMARY

Therefore it is a primary object of the present invention to provide a method for evaluation of cable aging degradation based on slice sampling in which an insulation layer of a cable is sliced and sampled to get specimens with different depths in the cable. Thus the difference of the aging degradation state between different positions such as an outer layer, a middle layer and an inner layer of the cable having accelerated aging degradation under influence of environmental factors can be learned.

It is another object of the present invention to provide a method for evaluation of cable aging degradation based on slice sampling by which insulation slices are obtained. The insulation slices are thin pieces. Then various tests such as dielectric withstand test, insulation resistance measurement, elongation test, etc. are carried out on the insulation slices obtained in general laboratories. No expensive equipment that provides extra-high voltage is required for the tests. Thus the cost is reduced and the prevalence of the method is increased.

It is a further object of the present invention to provide a method for evaluation of cable aging degradation based on slice sampling in which test results are used to establish a model for predicting cable aging and further developing an early warning system for cables in industrial site. The method has high industrial applicability.

It is a further object of the present invention to provide a method for evaluation of cable aging degradation based on slice sampling by which test specimens are obtained easily and conveniently and the method has high flexibility in selecting a section of the cable required to be tested. Moreover, the method can be directly applied to cables at work.

In order to achieve the above objects, a method for evaluation of cable aging degradation based on slice sampling of the present invention includes following steps. First, select a cable that includes an insulation layer and at least one conductive core. The conductive core is held by the insulation layer. Then second, cut the insulation layer from the outside in to get a first insulation slice and form a cut on the insulation layer. Within the cut, cut the insulation layer from the outside in again to get a second insulation slice. Next, compare the first insulation slice with the second insulation slice to get a difference of withstand voltage between the two insulation slices. Moreover, in the step of cutting the insulation layer from the outside in to get a first insulation slice, the step can be modified to cut the insulation layer from the outside in to get an insulation slice. Then cut a lateral surface of the insulation slice to split the insulation slice vertically into a first insulation slice and a second insulation slice. According to the steps mentioned above, samples of the insulation material with different depth in the cable are obtained and tested. Then the aging degradation state of the cable is evaluated by comparison of the difference between the test values of the samples.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein.

DETAILED DESCRIPTION

For better understanding of the features and effects of the present invention, refer to detail description of the following embodiments.

The cable operated in hostile environments has reduced service life due to accelerated aging, and the replacement time of the cable is difficult to predict. According to the risk of disasters/damages caused by short circuit is raised, thus the present invention provides a method for evaluation of cable aging degradation for better monitoring property changes of the cable.

Figure 1:
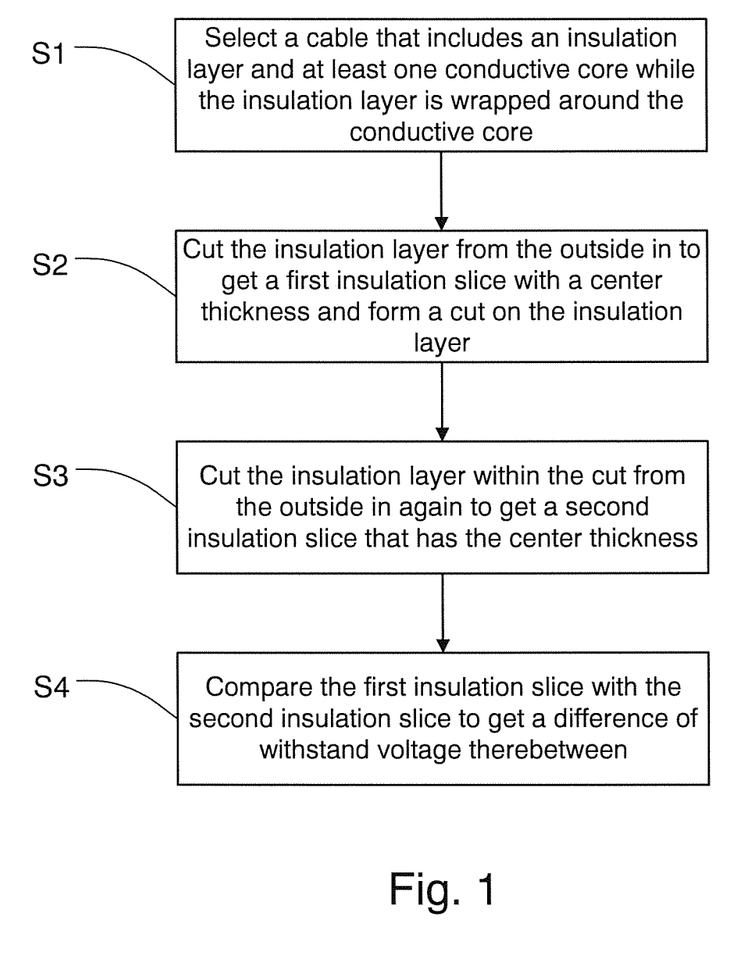
FIG. 1 is a flow chart showing steps of an embodiment according to the present invention.

Refer to FIG. 1, a flow chart of an embodiment according to the present invention is revealed. The method of the present invention includes following steps.

Step S1: Select a cable that includes an insulation layer and at least one conductive core while the insulation layer is wrapped around the conductive core.

Step S2: Cut the insulation layer from the outside in to get a first insulation slice with a center thickness and form a cut on the insulation layer.

Step S3: Cut the insulation layer within the cut from the outside in again to get a second insulation slice that has the center thickness.

Step S4: Compare the first insulation slice with the second insulation slice to get a difference of withstand voltage therebetween.

Figure 2:
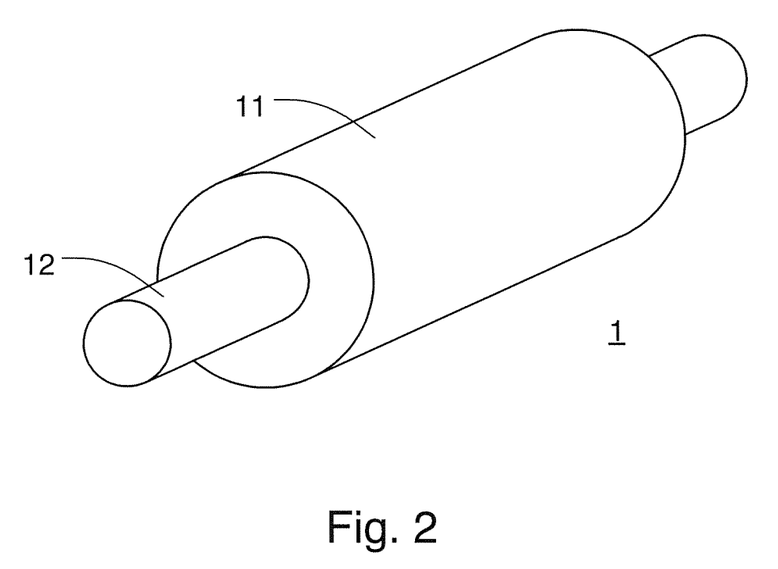
FIG. 2 is a schematic drawing showing structure of a cable of an embodiment according to the present invention.

In the step S1, the cable being tested is a wire used for transmission of electrical power and signals. Refer to FIG. 2, the inner side of a cable 1 is a conductive core 12 made from electrically conductive metal such as copper (Cu) or aluminum (Al). The selection of the material for the conductive core 12 depends on requirements of conductivity and cost.

The conductive core 12 is held by the insulation layer 11 made from insulation material such as rubber or plastic. The condition of the insulation material plays an important role on the service life of the cable. Whether there is an urgent need to replace the cable is determined according to the condition of the insulation material. Moreover, the present invention can not only be applied to a cable 1 with a single conductive core 12 but also the cable 1 with a plurality of conductive cores 12 since the test target is the insulation layer 11 for cover and insulation.

In the present invention, it is not necessary to cut a certain length of the cable tested and send the cable to a test place. The test section of the cable can be selected and sampled freely. For example, the section of the cable used within area underwater, with high radiation dose or at high temperate is selected and then is processed by the step S2, step S3 and the step S4. Even the cable that still works can be tested.

Figure 3:
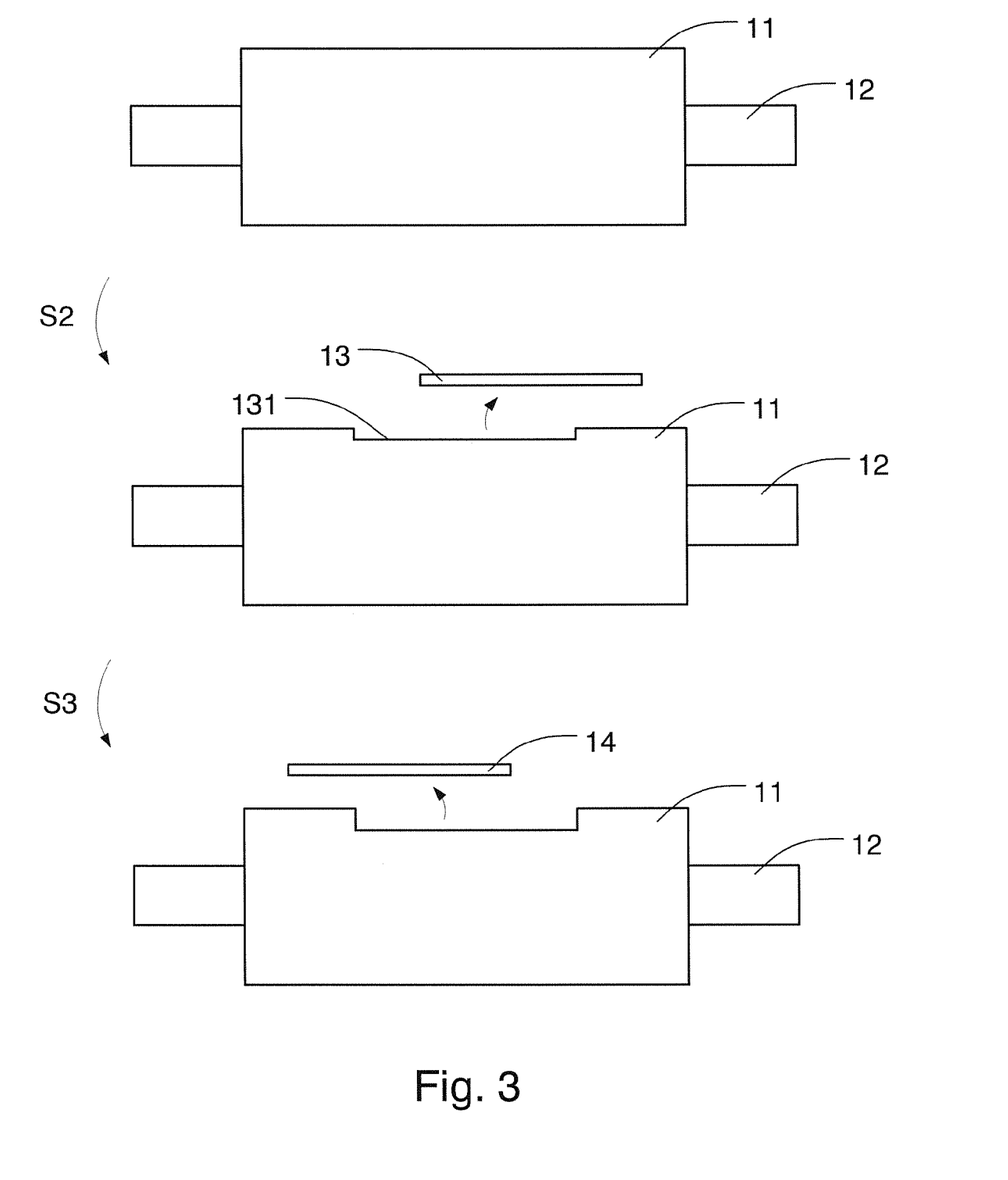
FIG. 3 shows step S 2 and step S3 of an embodiment according to the present invention.

In the step S2, the cable is sliced and sampled. Refer to FIG. 3, the insulation layer 11 of the selected cable is cut from the outside in to get a first insulation slice 13 that is a thin piece. At the same time, a cut 131 is formed on the insulation layer 11 being cut.

The first insulation slice 13 obtained is the part of the cable direct in contact with the fluid the cable soaked, the radiation or the high temperature. Due to the exposure, the first insulation slice 13 is with the highest aging rate and its properties have changed seriously such as embrittlement and cracking etc. Not only the structure of the first insulation slice 13 is damaged, the oxidation-resistant material on surface of the cable has also gradually degraded. The void characteristics in insulation materials such as size and density also have changed. The material for the insulation layer is getting easier to be invaded by water so that insulation resistance is reduced quickly. Thus the value of withstand voltage is significantly decreased and the cable may fail to work.

After obtaining the first insulation slice 13, run the step S3. Within the cut 131 formed on the first insulation slice 13, cut the insulation layer 11 from the outside in again to get a second simulation slice 14. As shown in FIG. 3, the second simulation slice 14 is getting closer to the conductive core 12 compared with the first insulation slice 13. Thus the accelerated aging degradation caused by environmental factors of the second simulation slice 14 is not as worse as the first insulation slice 13.

After getting the first insulation slice 13 and the second simulation slice 14, compare their value of withstand voltage with each other. For a new cable, the value of withstand voltage is ranging from 40 KV/mm to 60 KV/mm. After long-term use, the value of withstand voltage of the aged degraded cable is not as high as before. After being tested, it is found that the value of withstand voltage of the first insulation slice 13 is a bit smaller than the value of withstand voltage of the second simulation slice 14. By the difference and absolute value of withstand voltage, the aging and degradation of the specimens tested can be analyzed. Thus aging and degradation of sections with different depths in the cable can also be evaluated.

Figure 4:
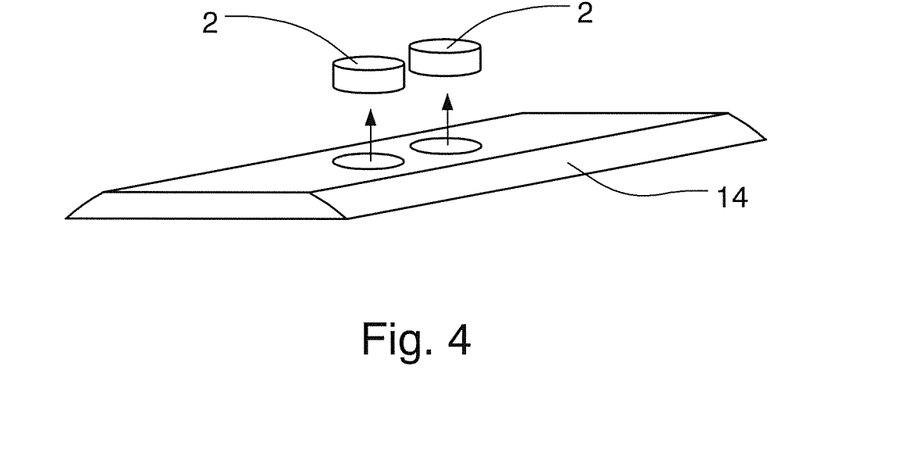
FIG. 4 is a schematic drawing showing cutting of a test slice of an embodiment according to the present invention.

In the present invention, make cuts of different depths in the insulation layer of the cable from the outside in to get a plurality of thin pieces. Then a center of each thin piece is used as the test target. As shown in FIG. 4, the second simulation slice 14 obtained is cut again to get several test specimens 2 with specific size and shape for performing various tests such as dielectric withstand test, insulation resistance measurement, elongation test, etc.

Figure 5:
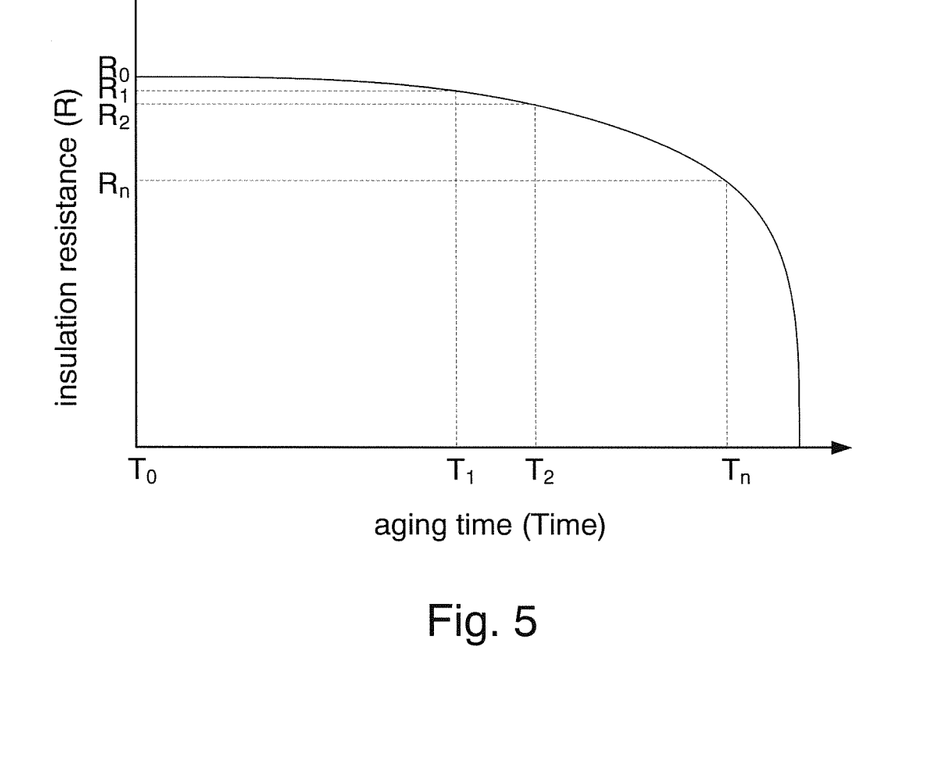
FIG. 5 shows the relation between aging time and insulation resistance of test specimens with the same depth in the cable of an embodiment according to the present invention.

The processes mentioned above show how the slice of the present invention is sampled. As to the aging and degradation condition of the cable, it is determined according to changes of data obtained by related tests. Take insulation resistance measurement as an example. As shown in FIG. 5, test specimens 2 of a cable at the same depth in the cable and different aging time are used to get a curve of insulation properties of the cable. The curve is drawn with insulation resistance (R) on the vertical axis and time (Time) on the horizontal axis. The curve shows that the longer the time, the lower the insulation resistance. After a certain point of the time, the insulation resistance is dropped dramatically. Technicians and staff members carried out tests can learn degree and extent of the aging at different times according to the curve. As to other tests such as dielectric withstand test, elongation test, etc., they are also carried out in similar ways to learn degree and extent of the cable degradation. Moreover, various tests are performed at the same aging time. Then the aging degradation state of the cable is learned more precisely by cross analysis of test results.

Figure 6:
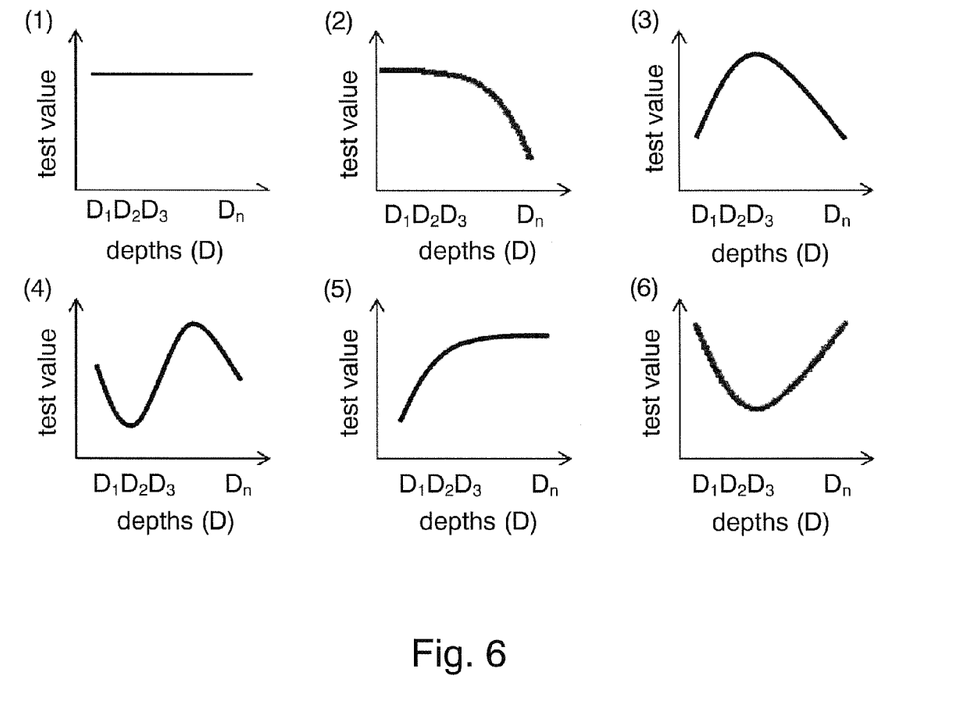
FIG. 6 shows relation between test results and depth of test specimens in a cable of the test specimens having the same aging time according to the present invention.

In addition, at the same aging time, carry out tests of the specimens with different depths in the cable. The results are shown in FIG. 6(1) to (6). The test specimens 2 with different depths (D) show various patterns, respectively representing different aging degradation state at difference depths in the cable.

By the present invention together with some special tests, a model for evaluating cable aging degradation is established easily and conveniently. For example, carry out the water immersion aging test with fixed parameters or the thermal aging test with fixed parameters on a new cable. Then get samples and perform tests according to the method of the present invention. Thus the relation between environmental parameters and cable aging degradation is revealed and a safety system for monitoring cable aging degradation and predicting service life is further derived.

In order to detect the cable suspected to have aging or degradation problem, only a part of the cable suspected to be damaged is sampled to have specimens for tests. Thus the operator can learn the degradation state of the cable and infer the causes.

In consideration of inventive mechanism of the present invention and requirements for industrial uses, the present invention is suitable for large cables with thicker insulation layers used in industrial site. The thickness is larger than 3 mm. For carrying voltage tests on the large cables, higher voltage is required to get a critical value the breakdown occurs. By slice sampling of the present invention, the first insulation slice 13 and the second insulation slice 14, both with center thickness smaller than 1 mm, are obtained to be tested. Thus the voltage applied in the dielectric withstanding test is significantly reduced and the test can be carried out in general labs. There is no need to use expensive high voltage equipment for testing the whole cable.

Figure 7:
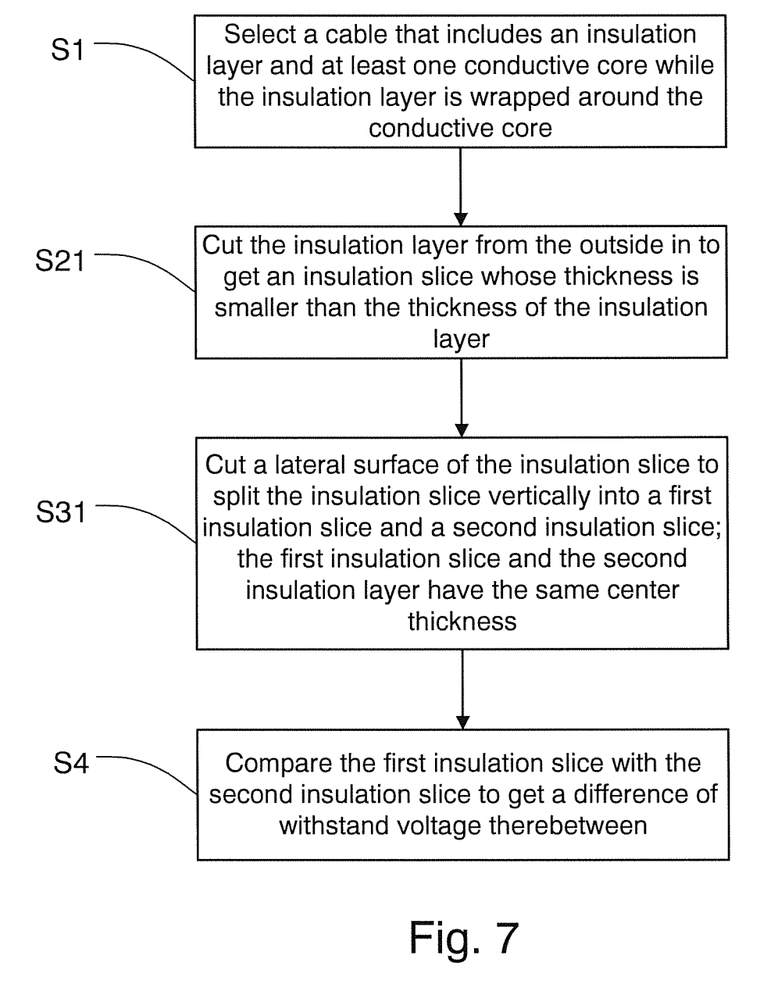
FIG. 7 is a flow chart showing steps of another embodiment according to the present invention.
Figure 8:
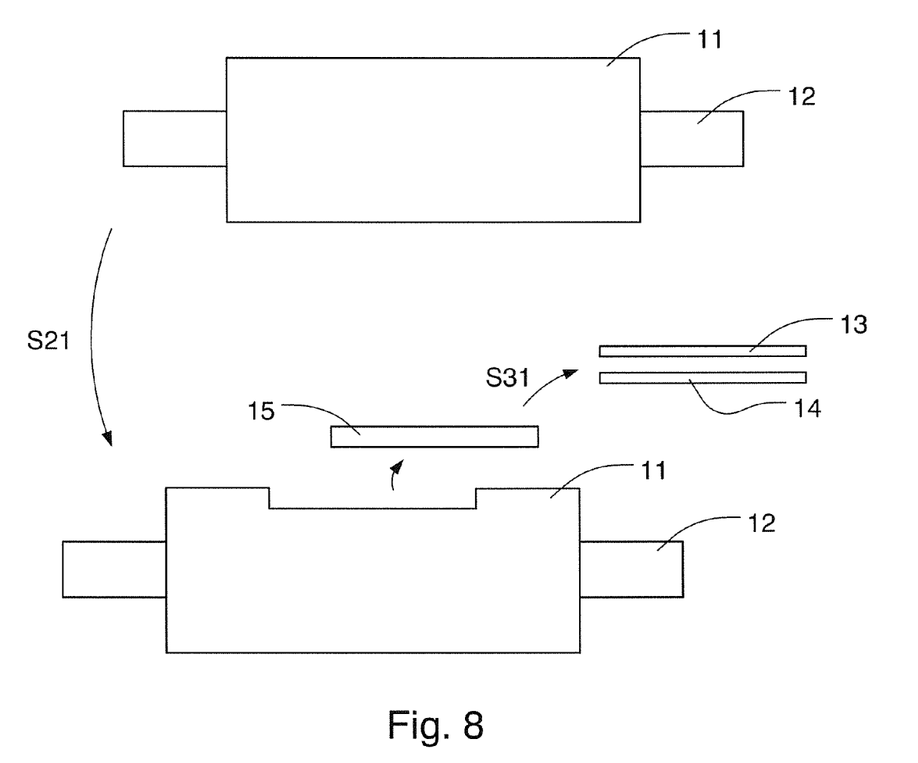
FIG. 8 shows step S 21 and step S31 of an embodiment according to the present invention.

Refer to FIG. 7 and FIG. 8, another embodiment of the present invention is revealed and having following steps.

Step S1: Select a cable that includes an insulation layer and at least one conductive core while the insulation layer is wrapped around the conductive core.

Step S21: Cut the insulation layer from the outside in to get an insulation slice whose thickness is smaller than the thickness of the insulation layer.

Step S31: Cut a lateral surface of the insulation slice to split the insulation slice vertically into a first insulation slice and a second insulation slice; the first insulation slice and the second insulation layer have the same center thickness.

Step S4: Compare the first insulation slice with the second insulation slice to get a difference of withstand voltage therebetween.

First get an insulation slice 15. Then cut and divide a lateral side of the insulation slice 15 into a first insulation slice 13 and a second insulation slice 14. Next carry on dielectric breakdown test and compare the dielectric strength of the first insulation slice 13 with that of the second insulation slice 14. The concept of this embodiment is the same as the above one. Both embodiments get specimens by slicing and perform tests on specimens having different depths in the cable so as to establish an evaluation model of the cable aging degradation.

Figure 9:
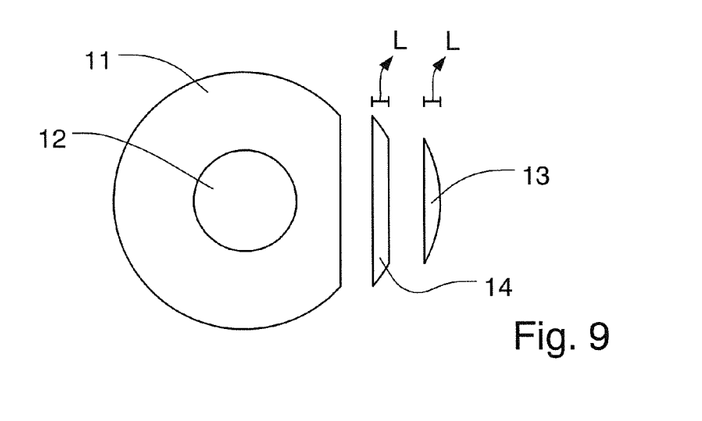
FIG. 9 is a sectional view showing thickness of a first insulation slice and of a second insulation slice of an embodiment according to the present invention.

Refer to FIG. 9, another sectional view of the cable 1 showing the first insulation slice 13 and the second insulation slice 14 is revealed. The appearance of the insulation splices 13, 14 is different due to different positions (depths) in the cable 1 but the center thickness L is the same. Thus in the step of comparing the first insulation slice 13 with the second insulation slice 14 to get a difference of withstand voltage therebetween, the breakdown voltage value of a portion of the cable 1 with the center thickness L obtained is an effective test result so as to set up a model for evaluation of the cable aging degradation. Moreover, a third insulation slice with the same center thickness L is further obtained by sampling under the second insulation slice 14 for voltage tests. Thus samples at an outer layer, a middle layer and an inner layer of the cable 1 are got. However, the total center thickness of all the slices obtained is smaller than the thickness of the insulation layer 11. That means the conductive 12 will not be exposed after completing slice sampling processes of the insulation layer 11.

In summary, the present invention sets up a model for detecting pattern and process of cable aging degradation by gradually cutting the insulation layer of the cable to get insulation slices with different depths in the cable. The slices at different depths have different degree and extent of degradation and the present invention features on that the dielectric withstanding test can be carried out in general labs due to the small thickness of the slices. The model can be further developed into an early warning system for cable aging degradation. The method is simple, easy and having widespread practical applications. Therefore the method of the present invention has both commercial and practical values.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

The invention claimed is:

1. A method for evaluation of cable aging degradation based on slice sampling comprising the steps of:
   selecting a cable that includes an insulation layer and at least one conductive core while the insulation layer is wrapped around the conductive core;

cutting the insulation layer from outside in to get a first insulation slice having a center thickness and form a cut on the insulation layer;

cutting the insulation layer within the cut from outside in again to get a second insulation slice having the center thickness; and comparing the first insulation slice with the second insulation slice to get a difference of withstand voltage between the first insulation slice and the second insulation slice;

wherein a thickness of the insulation layer is twice larger than the center thickness.

2. The method as claimed in claim 1, wherein a thickness of the insulation layer is larger than 3 mm.

3. The method as claimed in claim 1, wherein the center thickness is smaller than 1 mm.

4. The method as claimed in claim 1, wherein in the step of cutting the insulation layer from the outside in to get a first insulation slice and in the step of cutting the insulation layer within the cut from the outside in again to get a second insulation slice, the cable is at work.

5. The method as claimed in claim 1, wherein the insulation layer is made from rubber or plastic.

6. The method as claimed in claim 1, wherein in the step of comparing the first insulation slice with the second insulation slice to get a difference of withstand voltage between the first insulation slice and the second insulation slice, a breakdown voltage of a part of the first insulation slice with the center thickness and a breakdown voltage of a part of the second insulation slice with the center thickness are detected.

7. The method as claimed in claim 1, wherein before the step of comparing the first insulation slice with the second insulation slice to get a difference of withstand voltage between the first insulation slice and the second insulation slice, the method further includes a step of cutting the first insulation slice and the second insulation slice into at least one test specimen respectively and use the specimens for comparing.

8. A method for evaluation of cable aging degradation based on slice sampling comprising the steps of:

selecting a cable that includes an insulation layer and at least one conductive core while the insulation layer is wrapped around the conductive core;

cutting the insulation layer from outside in to get an insulation slice and a thickness of the insulation slice is smaller than a thickness of the insulation layer;

cutting a lateral surface of the insulation slice to split the insulation slice vertically into a first insulation slice and a second insulation slice; the first insulation slice and the second insulation layer have the same center thickness; and comparing the first insulation slice with the second insulation slice to get a difference of withstand voltage between the first insulation slice and the second insulation slice.

* * * * *